(12) United States Patent
Al-Sinan (10) Patent No.: US 11,815,500 B2
(45) Date of Patent: Nov. 14, 2023

(54) GAS DETECTOR CALIBRATION KIT AND INTEGRATED CARRIER

(71) Applicant: Saudi Arabian Oil Company, Dhahran (SA)

(72) Inventor: Hassan Shaker Ali Al-Sinan, Al-Qatif (SA)

(73) Assignee: Saudi Arabian Oil Company, Dhahran (SA)

( * ) Notice: Subject to any disclaimer, the term of this patent is extended or adjusted under 35 U.S.C. 154(b) by 261 days.

(21) Appl. No.: 17/467,845

(22) Filed: Sep. 7, 2021

(65) Prior Publication Data

US 2023/0072891 A1   Mar. 9, 2023

(51) Int. Cl.
*G01N 33/00* (2006.01)
*F17C 13/08* (2006.01)

(52) U.S. Cl.
CPC ....... *G01N 33/0006* (2013.01); *F17C 13/084* (2013.01); *F17C 2201/0104* (2013.01); *F17C 2205/0107* (2013.01); *F17C 2205/0323* (2013.01); *F17C 2250/0447* (2013.01)

(58) Field of Classification Search
CPC .............. G01N 33/0006; F17C 13/084; F17C 2201/0104; F17C 2205/0107; F17C 2205/0323; F17C 2250/0447
See application file for complete search history.

(56) References Cited

U.S. PATENT DOCUMENTS

| 4,486,044 A | 12/1984 | Gordon et al. |
|---|---|---|
| 4,832,398 A | 5/1989 | Tecca et al. |
| 9,423,077 B2 | 8/2016 | Adelman |
| 2004/0074279 A1* | 4/2004 | Forrest ............... G01N 33/0006 702/100 |
| 2005/0000981 A1* | 1/2005 | Peng .................... G01N 21/278 222/3 |

(Continued)

FOREIGN PATENT DOCUMENTS

| CN | 202812792 U | 3/2013 |
|---|---|---|
| CN | 205065289 U | 3/2016 |
| CN | 108679445 A | 10/2018 |

(Continued)

*Primary Examiner* — Andre J Allen
(74) *Attorney, Agent, or Firm* — DINSMORE & SHOHL LLP (57) ABSTRACT

An integrated carrier for a calibration gas storage cylinder is provided. The integrated carrier may comprise a carrier base, a carrier cap, and carrier beams. Each of the carrier beams may comprise a cap-end and a base-end. A cap-end bolt may be threaded into the cap-end and a base-end bolt may be threaded into the base-end. The carrier cap may comprise a laterally-oriented keyhole access opening that may be configured to mate with the cap-end of the carrier beams and the carrier base may comprise an axially-oriented bolt passage that may be configured to pass the base-end bolt of the carrier beams. The carrier base, the carrier cap, and the carrier beams may collectively define a cylindrical receiving space that may include the calibration gas storage cylinder and may define a longitudinal containment height. The carrier base may comprise a regulator-receiving depression and a detector-receiving depression that may each comprise open sides facing the carrier cap.

16 Claims, 6 Drawing Sheets

(56) References Cited

U.S. PATENT DOCUMENTS

2007/0178015 A1* 8/2007 Schaedlich ........ G01N 33/0006
                                                                         422/562
2019/0137465 A1* 5/2019 Mizutani ............ G01N 33/0016

FOREIGN PATENT DOCUMENTS

| EP | 1630471 | B1 | | 12/2007 | | |
|---|---|---|---|---|---|---|
| EP | 4105655 | A1 | * | 12/2022 | ......... | G01N 33/0006 |
| GB | 2415038 | A | * | 12/2005 | ......... | G01N 33/0006 |
| JP | 2016090024 | A | | 5/2016 | | |

* cited by examiner

GAS DETECTOR CALIBRATION KIT AND INTEGRATED CARRIER

BACKGROUND

The present disclosure relates to gas detection system testing and, more particularly, to gas calibration kits for use therein. Typically, gas cylinders are carried by hand while performing various testing activities at a site. Conventional methodology can be rudimentary and inefficient, since it is difficult to carry the tools and supplies necessary to conduct testing, e.g., at various locations that are only accessible with a ladder.

BRIEF SUMMARY

The subject matter of the present disclosure fills the logistical gaps in the current methodology of executing gas detection system testing. The invention aids in carrying out critical gas detection system activities by creating a comprehensive solution that integrates a calibration gas cylinder with its associated parts and supplies. In accordance with one embodiment of the present disclosure, a gas detector calibration kit is provided comprising a calibration gas storage cylinder, a gas flow regulator, a gas detector, and an integrated carrier comprising a carrier base, a carrier cap, and carrier beams extending longitudinally from the carrier base to the carrier cap. The carrier beams may be secured to the carrier cap and the carrier base with locking nuts. Additionally, in another embodiment, the gas calibration kit may include a magnet.

The carrier base, the carrier cap, and the carrier beams may collectively define a cylindrical receiving space that is laterally confined at the carrier cap, laterally and axially confined at the carrier base, and laterally open between the carrier cap and the carrier base. The cylindrical receiving space of the integrated carrier contains the calibration gas storage cylinder and defines a longitudinal containment height c such that $$\frac{1}{2}h < c < h.$$

The carrier base may comprise a regulator-receiving depression that is large enough to accommodate a majority of the gas flow regulator and comprises an open side facing the carrier cap. The carrier base may comprise a detector-receiving depression that is large enough to accommodate a majority of the gas detector and comprises an open side facing the carrier cap. The gas flow regulator may comprise a fitting that mates with the outlet fitting of the calibration gas storage cylinder and a regulator body portion that mates with the regulator-receiving depression of the carrier base. The gas detector may comprise a detector body portion that mates with the detector-receiving depression of the carrier base.

In accordance with another embodiment of the present disclosure, an integrated carrier for a calibration gas storage cylinder is provided. The integrated carrier comprises a carrier base comprising a disk-shaped recess for laterally and axially confining the calibration gas storage cylinder, a carrier cap configured in a shape of a containment ring for laterally confining the calibration gas storage cylinder, and carrier beams extending longitudinally from the carrier base to the carrier cap.

The carrier beams may be opposed to each other at an angle of 180° and comprise a cap-end and a base-end. The cap-end of each of the carrier beams comprises a cap-end bolt threaded into the cap-end along a longitudinal axis of the carrier beams. The base-end of each of the carrier beams may comprise a base-end bolt threaded into the base-end along the longitudinal axis of the carrier beams. The carrier cap may comprise a laterally-oriented keyhole access opening that is configured to mate with the cap-end of the carrier beams. The carrier base may comprise an axially-oriented bolt passage that is configured to pass the base-end bolt of the carrier beams. The carrier base, the carrier cap, and the carrier beams may collectively define a cylindrical receiving space that is laterally confined at the carrier cap, laterally and axially confined at the carrier base, and laterally open between the carrier cap and the carrier base. The cylindrical receiving space of the integrated carrier may contain the calibration gas storage cylinder and defines a longitudinal containment height. The carrier base may comprise a regulator-receiving depression and a detector-receiving depression that each comprise open sides facing the carrier cap.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Calibration of gas detectors may be performed to determine whether these detectors are operating as intended, namely whether these detectors are able to detect the presence of a threshold concentration of one or more gases in an ambient environment. Such calibration is performed with the use of a calibration gas stored within a calibration cylinder. During calibration, the calibration gas cylinder may be connected to the gas detector and a known volume and concentration of a test calibration gas may be released, which may be detected by a gas detection sensor of the gas detector. If the gas detector accurately determines the volume and concentration of the test calibration gas, the gas detector may be determined as operating correctly, and if the gas detector fails to accurately determine the volume and concentration of the test gas, the gas detector may require repair or replacement. As the test gas or calibration gas stored within the calibration gas cylinder may be harmful, there is a need for an integrated carrier that enables safe transport of calibration gas cylinders and various accessories associated with the calibration gas cylinders. As described throughout, the present disclosure describes integrated carriers that are designed to enable individuals to safely transport the calibration gas cylinders to locations in which gas detectors are positioned, including locations that may be difficult to access.

Figure 1:
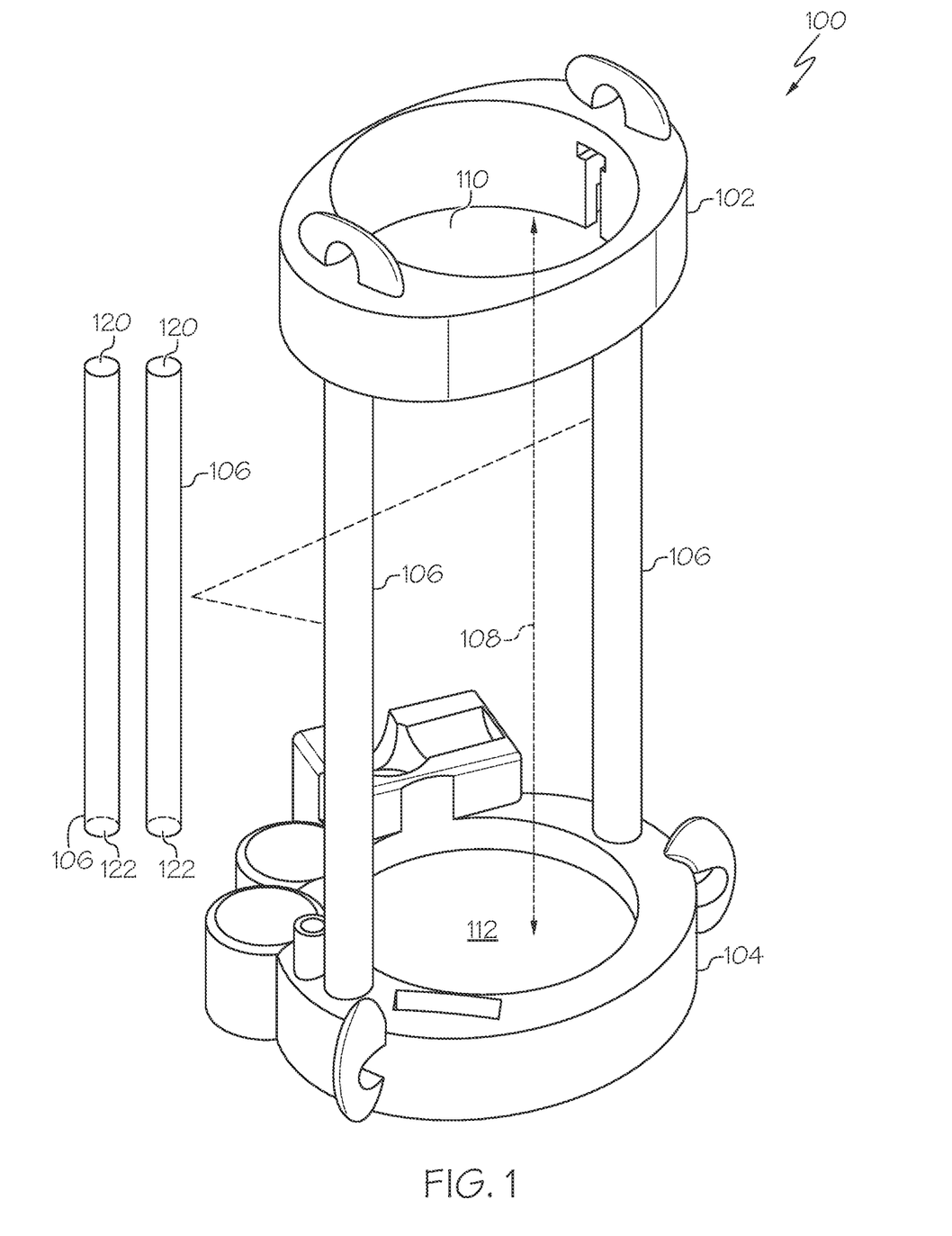
FIG. 1 is a schematic depiction of the integrated carrier.
Figure 2:
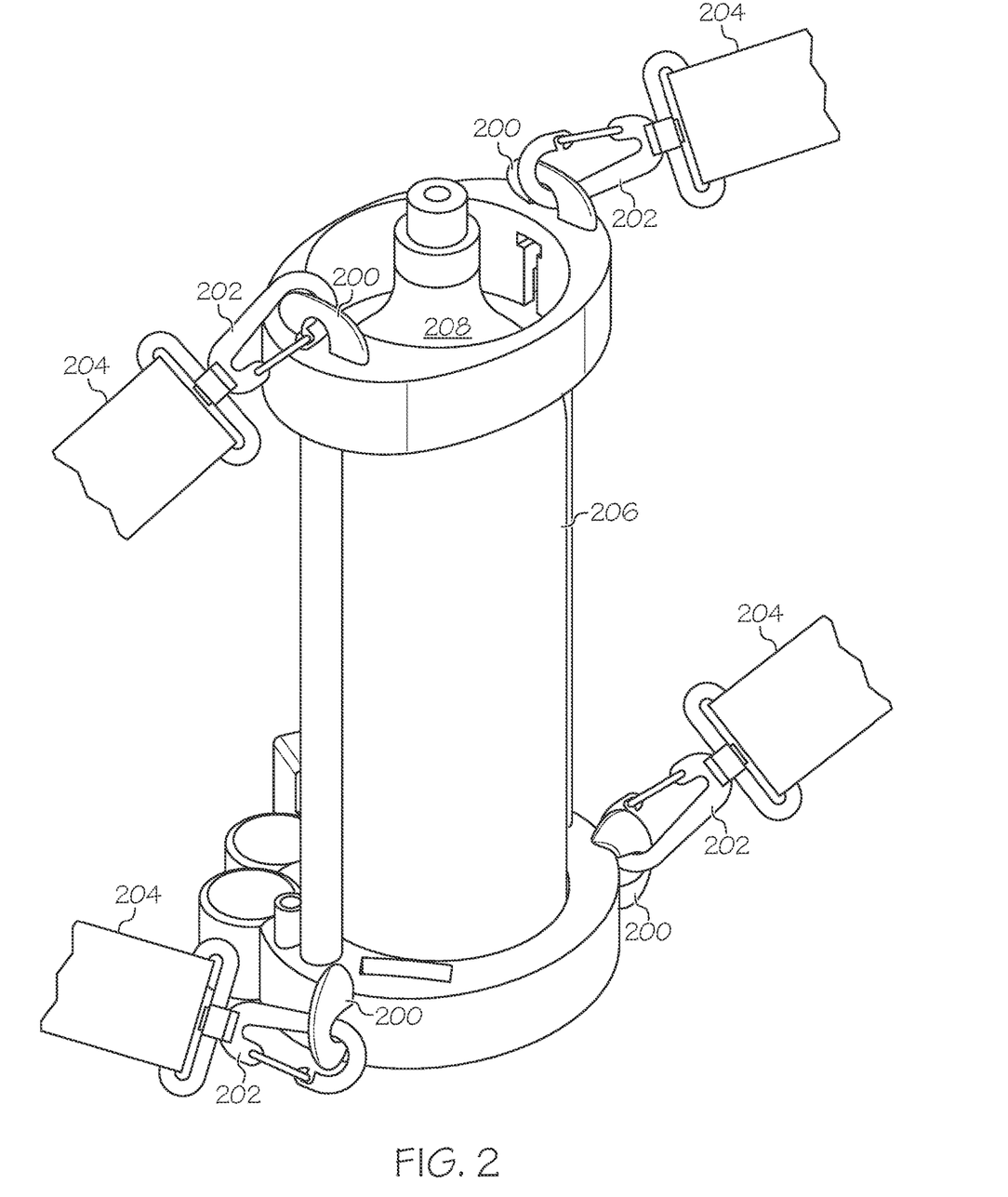
FIG. 2 is a schematic depiction of an integrated carrier with straps that may be attached to annular protrusions located on the integrated carrier.
Figure 3:
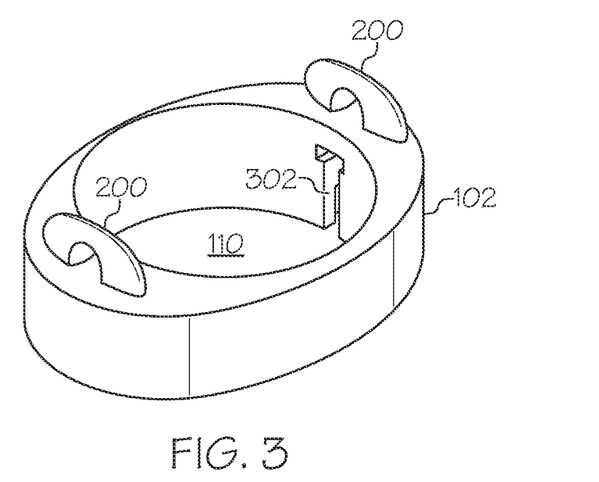
FIG. 3 is a schematic depiction of a carrier cap of the integrated carrier.
Figure 4:
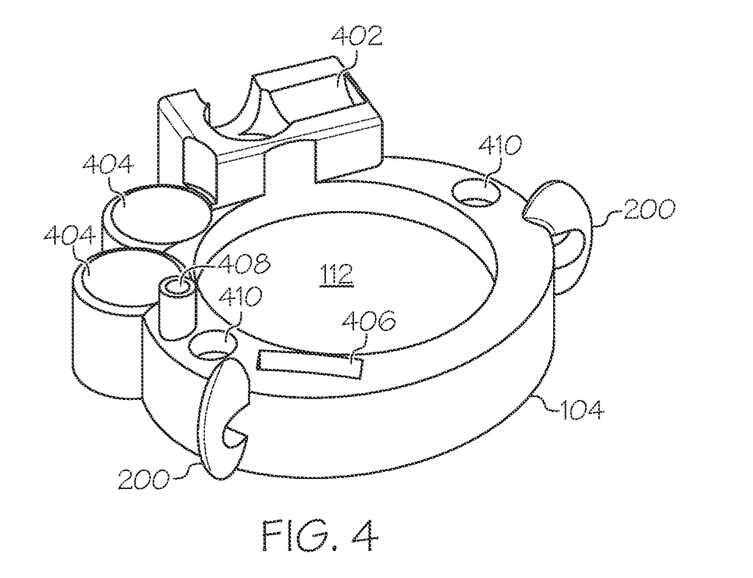
FIG. 4 is a schematic depiction of a carrier base of the integrated carrier.
Figure 5:
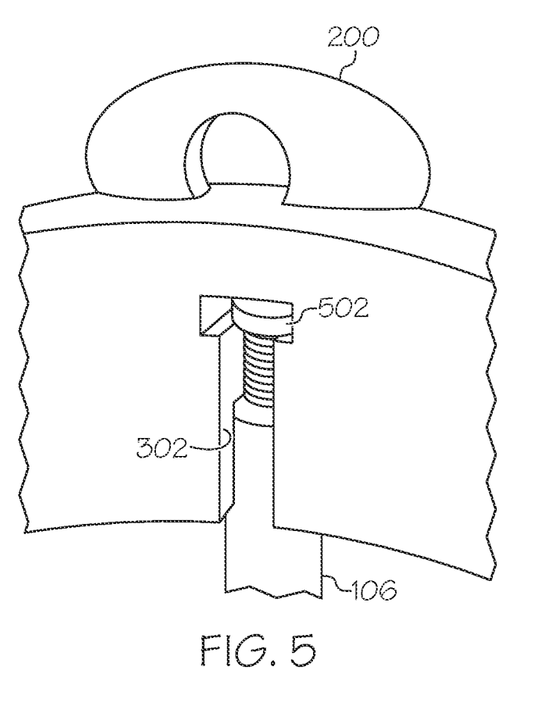
FIG. 5 is a schematic depiction of a cap-end of one of the carrier beams being secured to a keyhole access opening of the carrier cap.
Figure 6:
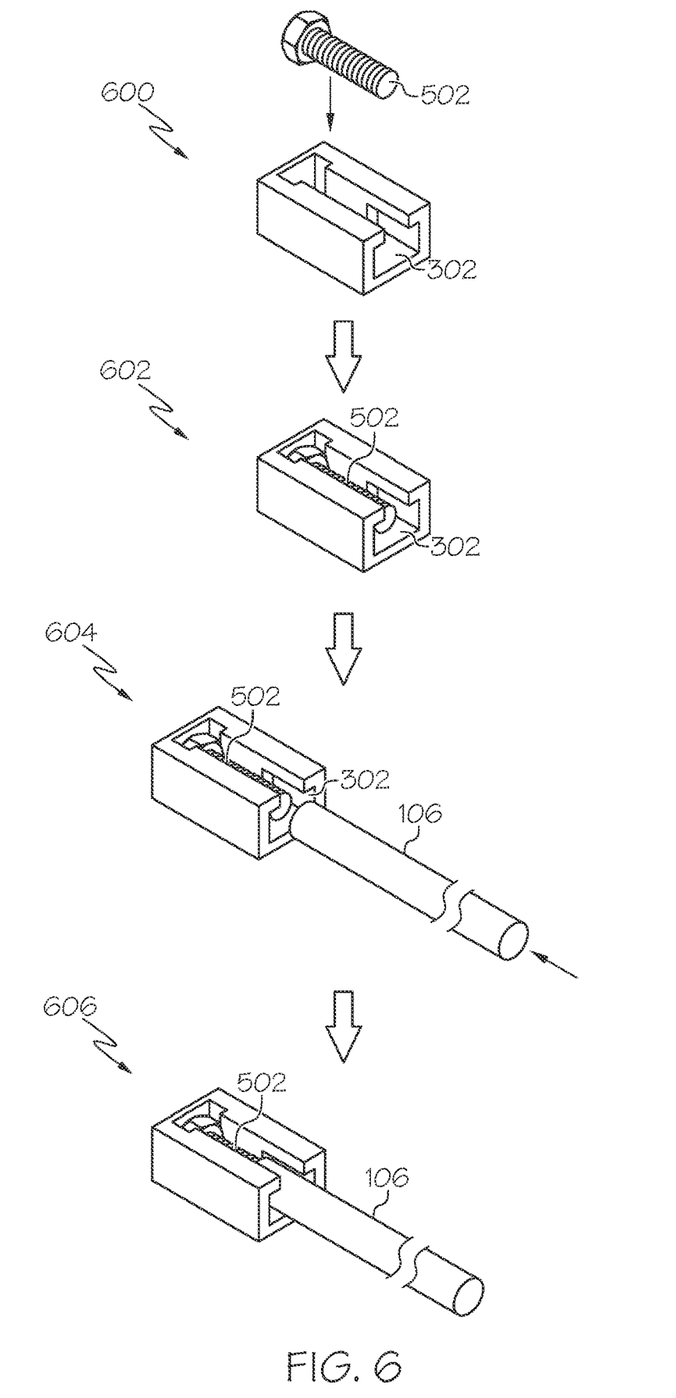
FIG. 6 include schematic depictions of an end of a carrier beam being secured to a keyhole access opening in the carrier cap of the integrated carrier.
Figure 7:
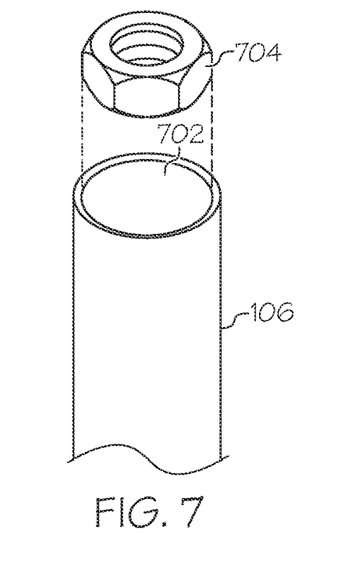
FIG. 7 is a schematic depiction of a cap end nut positioned within a carrier beam.
Figure 8:
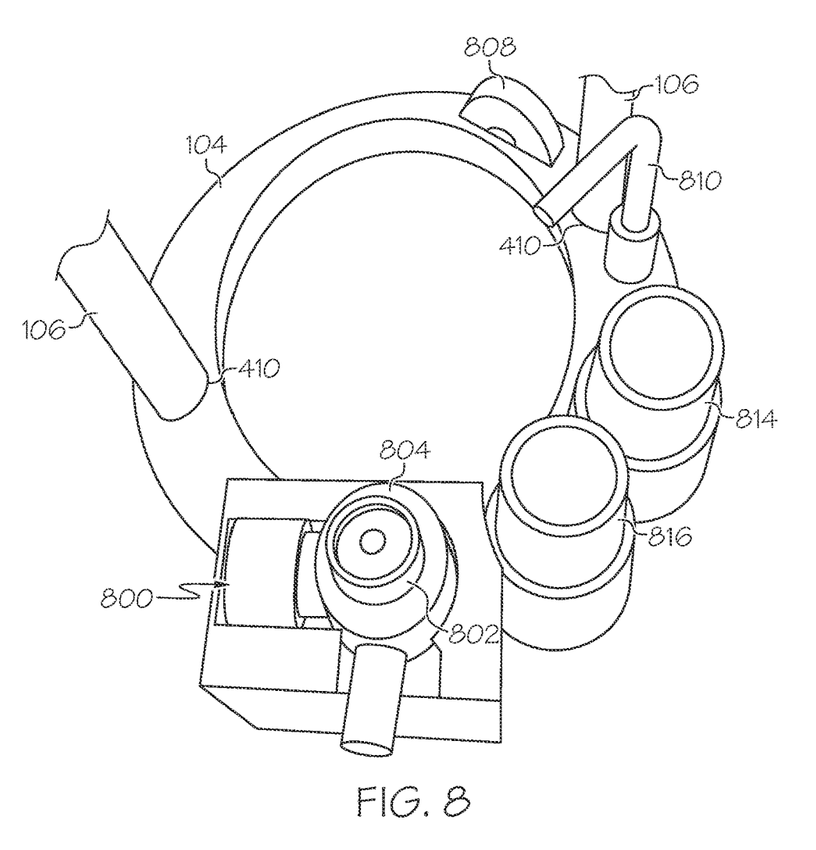
FIG. 8 is a schematic depiction of the carrier base in which sensors, regulators, carrier beams, and various other components are positioned.

Referring initially to FIGS. 1-8, an embodiment of an integrated carrier 100 for carrying a calibration gas storage cylinder 206 and various components of the integrated carrier 100 are schematically depicted. FIG. 1 is a schematic depiction of the integrated carrier 100. FIG. 2 is a schematic depiction of straps 204 attached to the integrated carrier 100. FIG. 3 is a schematic depiction of a carrier cap 102 of the integrated carrier 100. FIG. 4 is a schematic depiction of a carrier base 104 of the integrated carrier 100. FIG. 5 is a schematic depiction of a cap-end 120 of one of the carrier beams 106 being secured to a laterally oriented keyhole access opening of the carrier cap 102. FIG. 6 include schematic depictions of steps for securing an end of a carrier beam to an access opening of a carrier cap 102. FIG. 7 is a schematic depiction of a cap end nut positioned within one of the carrier beams 106. FIG. 8 is a schematic depiction of the carrier base 104 in which sensors, regulators, the carrier beams 106, and various other components are positioned.

Referring to FIG. 1, the integrated carrier 100 for carrying the calibration gas storage cylinder 206, as illustrated in FIG. 2, may comprise the carrier cap 102 in the shape of a containment ring 110 for laterally confining the calibration gas storage cylinder 206. The integrated carrier 100 may also include the carrier base 104 that may comprise a disk-shaped recess 112 for laterally and axially confining the calibration gas storage cylinder 206. The carrier cap 102 and the carrier base 104 may be made of a polylactic acid, a.k.a. PLA. In embodiments, the carrier cap 102 may be built to have, e.g., a width of 103 millimeters, a length of 142 millimeters, and an inner radius of 46.76 millimeters. In embodiments, the carrier base 104 may be built to have, e.g., a length of 164.2 millimeters, a height of 49.99 millimeters, an inner radius of 46.76 millimeters, and a depth of 12.5 millimeters.

The integrated carrier 100 may also include the carrier beams 106, which extend longitudinally from the carrier base 104 to the carrier cap 102. The carrier beams 106 are opposed to each other at an angle of 180 degrees. Additionally, the carrier beams 106 may comprise n carrier beams (e.g., 2 carrier beams) circumferentially opposed at an angular spacing θ, where θ=360°/n. As illustrated in FIG. 1, the carrier beams 106 may comprise a cylindrical body portion and each of the carrier beams 106 may further comprise a cap-end 120 and a base-end 122. The cap-end 120 and the base-end 122 may have a circular shape protruding from the cylindrical body portion of the carrier beam. In embodiments, the cap-end 120 and the base-end 122 may have other shapes as well, e.g., oval. Additionally, in embodiments, the carrier beams 106 may be designed to have different shapes and dimensions in order to accommodate a plurality of calibration gas storage cylinders of varying heights h' according to the relation:

$$\frac{1}{2}h' < c < h'.$$

Each of the carrier beams 106 may be formed of stainless steel. The carrier beams 106 may have a thickness of 1.5 millimeters and a height of 28 millimeters, and the cap-end 120 and the base-end 122 may have a diameter of, e.g., 12.7 millimeters. The carrier cap 102, the carrier base 104, and the carrier beams 106 collectively define a cylindrical receiving space 108 that is laterally confined at the carrier cap 102, axially confined at the carrier base 104, and laterally open between the carrier cap 102 and the carrier base 104.

Referring to FIG. 2, the carrier cap 102 and the carrier base 104 may include annular protrusions 200 disposed thereupon. In embodiments, a plurality of hooks 202 may be detachably coupled with the annular protrusions 200, and a plurality of straps 204 may be detachably coupled to the plurality of hooks 202. The plurality of straps 204 may be utilized to carry the integrated carrier 100 from one location to another with ease. The cylindrical receiving space 108 may contain a calibration gas storage cylinder 206, which may define a longitudinal containment height c such that $$\frac{1}{2}h < c < h.$$

In embodiments, a circumferential span between the carrier beams 106 is open such that a majority of the outer surface 208 of the calibration gas storage cylinder 206 is visible. It is noted that the straps 204 may be formed of fabric and stainless-steel joints of flexible lengths and sizes.

Referring to FIG. 3, the carrier cap 102 is illustrated as including the annular protrusions 200 that extend from two areas on a top surface of the carrier cap 102. The carrier cap 102 may also include a laterally-oriented keyhole access opening 302 that is configured to receive a cap-end 120 of each of the carrier beams 106. The carrier cap 102 is configured in the shape of the containment ring 110 and forms a circumferential gap between an outer diameter of the calibration gas storage cylinder 206 and an internal diameter of the carrier cap 102. The circumferential gap may be in the range of 15-20 millimeters. In embodiments, the internal diameter of the carrier cap 102 is selected to allow for a relatively secure fit between the outer diameter of the calibration gas storage cylinder 206 and the internal diameter of the carrier cap 102, while permitting removal of the calibration gas storage cylinder 206 through the carrier cap 102 along a longitudinal axis of the calibration gas storage cylinder 206.

Referring to FIG. 4, the carrier base 104 may comprise a disk-shaped recess 112 for laterally and axially confining the calibration gas storage cylinder 206. The carrier base 104 may include a variety of depressions and passages. In embodiments, the carrier base 104 may include a regulator-receiving depression 402 and a detector-receiving depression that each comprise open sides facing the carrier cap 102. The regulator-receiving depression 402 may be large enough to accommodate a majority of a gas flow regulator and the detector-receiving depression may be large enough to accommodate a majority of a gas detector. In embodiments, the regulator-receiving depression 402 may be formed of PLA and a part of the depression may have the dimensions of, e.g., a length of 54.99 nanometers, a width of 38 millimeters, an inner radius of 27 millimeters, and a depth of 53.5 millimeters. Additionally, another part of the depression—the part that accommodates a knob of a regulator that is external to the integrated carrier 100—may have, e.g., a width of 18 millimeters, a length of 25 millimeters, and a height of 8 millimeters. The regulator-receiving depression 402 may include a concave portion having a radius that matches an outer diameter of a body of a regulator that may be positioned in the depression. It is noted that a depression that "accommodates a majority" of another object is simply intended to denote that most of the object's body will fit within the depression. As a result, the object will tend to remain contained within the depression as the object in which the depression is formed moves.

In embodiments, the regulator-receiving depression 402 may be designed to have dimensions such that the body of a regulator may be positioned within the concave portion of the regulator-receiving depression 402. The regulator may be positioned within the regulator-receiving depression 402 such that the regulator may be positioned tightly within the regulator-receiving depression 402 so as to prevent any movement of the regulator while the integrated carrier 100 is being transported. The carrier base 104 may also comprise sensor-receiving depressions 404. Additionally, the body of the regulator may fit within the concave portion of the regulator-receiving depression 402 such that placement and remove of the regulator is facilitated. The carrier base 104 may also include additional storage receiving depressions, e.g., a magnet receiving depression 406, an Allen key receiving depression 408, and/or combinations thereof. The carrier base 104 may also include an axially-oriented bolt passages 410 positioned at various locations on the top surface of the carrier base 104. The carrier base 104 may include an axially-oriented bolt passages 410 that is configured to pass base-end bolts the carrier beams 106. The magnet receiving depression 406 may be formed to have, e.g., a length of 31.99 millimeters, a width of 7.51 millimeters, and a height of 18 millimeters. The Allen key receiving depression 408 may be formed to have a length of 5.75 millimeters, a width of 5.75 millimeters, and a depth of 46.44 millimeters. Additionally, the sensor-receiving depressions 404 may have an inner radius of 15.51 millimeters and a height of 28 millimeters.

Referring to FIG. 5, a cap-end 120 of one of the carrier beams 106 is illustrated as being secured to the carrier cap 102 by being positioned within the laterally-oriented keyhole access opening 302. In particular, the laterally-oriented keyhole access opening 302 is configured to mate with the cap-end 120 of each of the carrier beams 106 with the use of a cap-end bolt 502 and a cap-end nut. Each of the carrier beams 106 may comprise a cap-end bolt 502 threaded into the cap-end 120 of each of the carrier beams 106 along a longitudinal axis of each the carrier beams 106 using the cap-end bolt 502. Additionally, the base-end 122 of each of the carrier beams 106 may comprise a bolt-end bolt (not shown) threaded into each of the base-end 122 of each of the carrier beams 106 along a longitudinal axis of the carrier beams 106 with the use of a base-end bolt. The base-end bolt may have the shape and dimensions that are comparable to the cap-end bolt 502. The cap-end bolt 502 and the base-end bolt may be formed of stainless steel. In embodiments, the cap-end bolt 502, the base-end bolt, the cap-end nut, and the base-end nut may be, e.g., a Hex Bolt A4-70 and a Hex Nut A4-70.

Referring to FIG. 6, the steps of securing one of the carrier beams 106 to the carrier cap 102 is illustrated. Specifically, in step 600, a portion of the carrier cap 102 is illustrated as including a laterally-oriented keyhole access opening 302 in which a cap-end bolt 502 may be positioned. The laterally-oriented keyhole access opening 302 may have dimensions such that a top part of the laterally-oriented keyhole access opening 302 may be designed to accommodate the head of the cap-end bolt 502. In step 602, the cap-end bolt 502 is shown to be positioned within the laterally-oriented keyhole access opening 302. In step 604, the cap-end 120 of one of the carrier beams 106 is illustrated in a position close to the cap-end bolt 502. It is noted that the cap-end 120 may include a cap-end nut receiving aperture in which a cap-end nut may be positioned. In step 606, the cap-end bolt 502 may be tightened within the laterally-oriented keyhole access opening 302 by imparting a relative rotation between the cap-end bolt 502 and one of the carrier beams 106.

For example, the relative rotation may be achieved by either turning the cap-end bolt 502 or one of the carrier beams 106 in a clockwise direction. Based on the rotation, a cap-end nut disposed in the cap-end 120 of each of the carrier beams 106 may mechanically couple with the cap-end bolt 502 disposed in the portion, thereby securing each carrier beam to the carrier cap 102. Similarly, a base-end nut disposed in the base-end 122 of each of the carrier beams 106 may mechanically couple with respective base-end bolts disposed in a base-end nut receiving aperture disposed in the base-end 122. In this way, the base-end 122 of each of the carrier beams 106 may be secured to the carrier base 104 of the integrated carrier 100.

In embodiments, the cap-end bolt 502 may be threaded into the laterally-oriented keyhole access opening 302 disposed on the carrier cap 102 according to a first orientation and the base-end bolt may be threaded into the another keyhole access opening on the carrier base 104 (not shown) according to a second orientation. The second orientation may be diametrically opposed to the first orientation.

Referring to FIG. 7, the cap-end 120 and the base-end 122 of each of the carrier beams 106 may comprise a cap-end nut receiving aperture 702 and the base-end nut receiving aperture (not shown). The cap-end nut receiving aperture 702 may accommodate a cap-end nut 704 that is configured to mate with the cap-end bolt 502 as illustrated in FIGS. 5 and 7. In embodiments, the cap-end nut 704, by mating with the cap-end bolt 502, may secure the cap-end 120 of each of the carrier beams 106 in respective laterally-oriented keyhole access openings (e.g., the laterally-oriented keyhole access opening 302) disposed in the carrier cap 102.

Referring to FIG. 8, various components may be positioned within various depressions and disposed in the carrier base 104 of the integrated carrier 100 of the present disclosure. Specifically, FIG. 8 depicts a gas flow regulator 800 that is accommodated by the regulator-receiving depression 402. The gas flow regulator 800 may comprise a fitting 802 that mates with the outlet fitting 210 of the calibration gas storage cylinder 206. Additionally, a regulator body portion 804 of the gas flow regulator 800 may mate with the regulator-receiving depression 402 of the carrier base 104. Additionally, a magnet 808 may be positioned within the magnet receiving depression 406 and an Allen key 810 may be positioned within the Allen key receiving depression 408 disposed in the carrier base 104. The carrier beams 106 may be positioned within the axially-oriented bolt passages 410 and sensors 814 and 816 may be positioned within the sensor-receiving depressions 404.

It should be understood that embodiments of the present disclosure are directed to a gas detector calibration kit comprising a calibration gas storage cylinder, a gas flow regulator, a gas detector, and an integrated carrier, wherein the calibration gas storage cylinder contains a calibration gas, comprises an outlet fitting, and defines a longitudinal cylinder height h, the integrated carrier comprises a carrier base, a carrier cap, and carrier beams extending longitudinally from the carrier base to the carrier cap, the carrier base, the carrier cap, and the carrier beams collectively define a cylindrical receiving space that is laterally confined at the carrier cap, laterally and axially confined at the carrier base, and laterally open between the carrier cap and the carrier base, the cylindrical receiving space of the integrated carrier contains the calibration gas storage cylinder and defines a longitudinal containment height c such that $$\frac{1}{2}h < c < h,$$

the carrier base comprises a regulator-receiving depression that is large enough to accommodate a majority of the gas flow regulator and comprises an open side facing the carrier cap, the carrier base comprises a detector-receiving depression that is large enough to accommodate a majority of the gas detector and comprises an open side facing the carrier cap, the gas flow regulator comprises a fitting that mates with the outlet fitting of the calibration gas storage cylinder and a regulator body portion that mates with the regulator-receiving depression of the carrier base, and the gas detector comprises a detector body portion that mates with the detector-receiving depression of the carrier base. It is noted that the gas detector calibration kit may comprises a plurality of pairs of differently-sized carrier beams to accommodate a plurality of calibration gas storage cylinders of varying heights h' according to a relation;

$$\frac{1}{2}h' < c < h'.$$

One or more aspects of the present disclosure are described herein. A first aspect may include a gas detector calibration kit comprising a calibration gas storage cylinder, a gas flow regulator, a gas detector, and an integrated carrier, wherein: the calibration gas storage cylinder contains a calibration gas, comprises an outlet fitting, and defines a longitudinal cylinder height h, the integrated carrier comprises a carrier base, a carrier cap, and carrier beams extending longitudinally from the carrier base to the carrier cap, the carrier base, the carrier cap, and the carrier beams collectively define a cylindrical receiving space that is laterally confined at the carrier cap, laterally and axially confined at the carrier base, and laterally open between the carrier cap and the carrier base, the cylindrical receiving space of the integrated carrier contains the calibration gas storage cylinder and defines a longitudinal containment height c such that $$-\frac{1}{2}h < c < h,$$

the carrier base comprises a regulator-receiving depression that is large enough to accommodate a majority of the gas flow regulator and comprises an open side facing the carrier cap, the carrier base comprises a detector-receiving depression that is large enough to accommodate a majority of the gas detector and comprises an open side facing the carrier cap, the gas flow regulator comprises a fitting that mates with the outlet fitting of the calibration gas storage cylinder and a regulator body portion that mates with the regulator-receiving depression of the carrier base, and the gas detector comprises a detector body portion that mates with the detector-receiving depression of the carrier base.

A second aspect may include the first aspect, wherein each of the carrier beams comprises a cap-end and a base-end, the cap-end of each of the carrier beams comprises a cap-end bolt threaded into the cap-end along a longitudinal axis of the carrier beams, the base-end of each of the carrier beams comprises a base-end bolt threaded into the base-end along the longitudinal axis of the carrier beams, the carrier cap comprises a laterally-oriented keyhole access opening that is configured to mate with the cap-end of each of the carrier beams, and the carrier base comprises an axially-oriented bolt passage that is configured to pass the base-end bolt of each of the carrier beams.

A third aspect may include either the first aspect or the second aspect, wherein the cap-end bolt is threaded into the cap-end according to a first orientation.

A fourth aspect may include the third aspect, wherein the base-end bolt is threaded into the base-end according to a second orientation.

A fifth aspect may include the fourth aspect, wherein the second orientation is diametrically opposed to the first orientation.

A sixth aspect may include either the first aspect or the second aspect, wherein the cap-end of each of the carrier beams comprises a cap-end nut receiving aperture, and the cap-end nut receiving aperture accommodates a cap-end nut that is configured to mate with the cap-end bolt of the carrier beams.

A seventh aspect may include either the first aspect or the second aspect or the third aspect, wherein each of the carrier beams comprises a cap-end and a base-end, the cap-end of each of the carrier beams comprises a cap-end bolt threaded into the cap-end along a longitudinal axis of the carrier beams, the base-end of each of the carrier beams comprises a base-end bolt threaded into the base-end of each the carrier beams along the longitudinal axis of the carrier beams, the carrier base comprises a laterally-oriented keyhole access opening that is configured to mate with the base-end of the carrier beams, and the carrier cap comprises an axially-oriented bolt passage that is configured to pass the cap-end bolt of the carrier beams.

An eight aspect may include any of the first to the fourth aspects, wherein the carrier beams are opposed to each other at an angle of 180 degrees.

A ninth aspect may include any of the first aspect or the second aspect or the third aspect, wherein the carrier beams comprise n carrier beams circumferentially opposed at an angular spacing θ, where θ=360°/n.

A tenth aspect may include any of the first aspect or the second aspect, wherein a circumferential span between the career beams is open such that a majority of an outer surface of the calibration gas storage cylinder is visible.

An eleventh aspect may include any of the first aspect or the second aspect or the third aspect, wherein each of the carrier beams comprises a cylindrical body portion.

A twelfth aspect may include any of the first aspect or the second aspect, wherein each of the cap-end and the base-end of each of the carrier beams has a circular shape protruding from the cylindrical body portion of the carrier beam.

A thirteenth aspect may include any of the first aspect or the second aspect or the third aspect, wherein the carrier cap is configured in a shape of a containment ring and forms a circumferential gap between an outer diameter of the calibration gas storage cylinder and an internal diameter of the carrier cap.

A fourteenth aspect may include any of the first aspect or the second aspect, wherein the carrier base comprises a disk-shaped recess for laterally and axially confining the calibration gas storage cylinder.

A fifteenth aspect may include any of the first aspect or the second aspect, wherein the gas detector calibration kit comprises a plurality of pairs of differently-sized carrier beams to accommodate a plurality of calibration gas storage cylinders of varying heights h' according to a relation:

$$\frac{1}{2}h' < c < h'.$$

A sixteenth aspect may include an integrated carrier for a calibration gas storage cylinder, the integrated carrier comprising: a carrier base comprises a disk-shaped recess for laterally and axially confining the calibration gas storage cylinder, a carrier cap configured in a shape of a containment ring for laterally confining the calibration gas storage cylinder, and carrier beams extending longitudinally from the carrier base to the carrier cap, wherein each of the carrier beams are opposed to each other at an angle of 180° and comprise a cap-end and a base-end, the cap-end of each of the carrier beams comprises a cap-end bolt threaded into the cap-end along a longitudinal axis of the carrier beams, the base-end of each of the carrier beams comprises a base-end bolt threaded into the base-end along the longitudinal axis of the carrier beams, the carrier cap comprises a laterally-oriented keyhole access opening that is configured to mate with the cap-end of the carrier beams, the carrier base comprises an axially-oriented bolt passage that is configured to pass the base-end bolt of the carrier beams, the carrier base, the carrier cap, and the carrier beams collectively define a cylindrical receiving space that is laterally confined at the carrier cap, laterally and axially confined at the carrier base, and laterally open between the carrier cap and the carrier base, the cylindrical receiving space of the integrated carrier contains the calibration gas storage cylinder and defines a longitudinal containment height, the carrier base comprises a regulator-receiving depression and a detector-receiving depression that each comprise open sides facing the carrier cap.

It is also noted that relations herein of "a plurality" of any one component, element, etc., should not be used to create an inference that the alternative use of the articles "a" or "an" should be limited to a single component, element, etc.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A gas detector calibration kit comprising:
a calibration gas storage cylinder containing a calibration gas, the storage cylinder comprising an outlet fitting and defining a longitudinal cylinder height h;
a gas flow regulator;
a gas detector; and
an integrated carrier comprising a carrier base, a carrier cap, and carrier beams extending longitudinally from the carrier base to the carrier cap,
the carrier base, the carrier cap, and the carrier beams collectively define a cylindrical receiving space that is laterally confined at the carrier cap, laterally and axially confined at the carrier base, and laterally open between the carrier cap and the carrier base,
the cylindrical receiving space of the integrated carrier contains the calibration gas storage cylinder and defines a longitudinal containment height c such that $$\frac{1}{2}h < c < h,$$

the carrier base comprises a regulator-receiving depression that is large enough to accommodate a majority of the gas flow regulator and comprises an open side facing the carrier cap,
the carrier base comprises a detector-receiving depression that is large enough to accommodate a majority of the gas detector and comprises an open side facing the carrier cap,
the gas flow regulator comprises a fitting that mates with the outlet fitting of the calibration gas storage cylinder and a regulator body portion that mates with the regulator-receiving depression of the carrier base, and
the gas detector comprises a detector body portion that mates with the detector-receiving depression of the carrier base.

2. The gas detector calibration kit of claim 1, wherein:
each of the carrier beams comprises a cap-end and a base-end;
the cap-end of each of the carrier beams comprises a cap-end bolt threaded into the cap-end along a longitudinal axis of the carrier beams;
the base-end of each of the carrier beams comprises a base-end bolt threaded into the base-end along the longitudinal axis of the carrier beams;
the carrier cap comprises a laterally-oriented keyhole access opening that is configured to mate with the cap-end of each of the carrier beams; and
the carrier base comprises an axially-oriented bolt passage that is configured to pass the base-end bolt of each of the carrier beams.

3. The gas detector calibration kit of claim 2, wherein the cap-end bolt is threaded into the cap-end according to a first orientation.

4. The gas detector calibration kit of claim 3, wherein the base-end bolt is threaded into the base-end according to a second orientation.

5. The gas detector calibration kit of claim 4, wherein the second orientation is diametrically opposed to the first orientation.

6. The gas detector calibration kit of claim 2, wherein:
the cap-end of each of the carrier beams comprises a cap-end nut receiving aperture; and
the cap-end nut receiving aperture accommodates a cap-end nut that is configured to mate with the cap-end bolt of the carrier beams.

7. The gas detector calibration kit of claim 1, wherein:
each of the carrier beams comprises a cap-end and a base-end;
the cap-end of each of the carrier beams comprises a cap-end bolt threaded into the cap-end along a longitudinal axis of the carrier beams;
the base-end of each of the carrier beams comprises a base-end bolt threaded into the base-end of each the carrier beams along the longitudinal axis of the carrier beams;
the carrier base comprises a laterally-oriented keyhole access opening that is configured to mate with the base-end of the carrier beams; and
the carrier cap comprises an axially-oriented bolt passage that is configured to pass the cap-end bolt of the carrier beams.

8. The gas detector calibration kit of claim 1, wherein the carrier beams are opposed to each other at an angle of 180°.

9. The gas detector calibration kit of claim 1, wherein the carrier beams comprise n carrier beams circumferentially opposed at an angular spacing θ, where θ=360°/n.

10. The gas detector calibration kit of claim 1, wherein a circumferential span between the carrier beams is open, such that a majority of an outer surface of the calibration gas storage cylinder is visible.

11. The gas detector calibration kit of claim 1, wherein each of the carrier beams comprises a cylindrical body portion.

12. The gas detector calibration kit of claim 11, wherein each of a cap-end and a base-end of each of the carrier beams has a circular shape protruding from the cylindrical body portion of each of the carrier beams.

13. The gas detector calibration kit of claim 1, wherein:
the carrier cap is configured in a shape of a containment ring and forms a circumferential gap between an outer diameter of the calibration gas storage cylinder and an internal diameter of the carrier cap; and
the circumferential gap is in a range of 15-20 millimeters.

14. The gas detector calibration kit of claim 1, wherein the carrier base comprises a disk-shaped recess for laterally and axially confining the calibration gas storage cylinder.

15. The gas detector calibration kit of claim 1, wherein the gas detector calibration kit comprises a plurality of pairs of differently-sized carrier beams to accommodate a plurality of calibration gas storage cylinders of varying heights h' according to a relation:

$$\frac{1}{2}h' < c < h'.$$

16. An integrated carrier for a calibration gas storage cylinder, the integrated carrier comprising:
a carrier base comprises a disk-shaped recess for laterally and axially confining the calibration gas storage cylinder;
a carrier cap configured in a shape of a containment ring for laterally confining the calibration gas storage cylinder; and
carrier beams extending longitudinally from the carrier base to the carrier cap, wherein
each of the carrier beams are opposed to each other at an angle of 180° and comprise a cap-end and a base-end,
the cap-end of each of the carrier beams comprises a cap-end bolt threaded into the cap-end along a longitudinal axis of the carrier beams,
the base-end of each of the carrier beams comprises a base-end bolt threaded into the base-end along the longitudinal axis of the carrier beams,
the carrier cap comprises a laterally-oriented keyhole access opening that is configured to mate with the cap-end of the carrier beams,
the carrier base comprises an axially-oriented bolt passage that is configured to pass the base-end bolt of the carrier beams,
the carrier base, the carrier cap, and the carrier beams collectively define a cylindrical receiving space that is laterally confined at the carrier cap, laterally and axially confined at the carrier base, and laterally open between the carrier cap and the carrier base,
the cylindrical receiving space of the integrated carrier contains the calibration gas storage cylinder and defines a longitudinal containment height, and
the carrier base comprises a regulator-receiving depression and a detector-receiving depression that each comprise open sides facing the carrier cap.

* * * * *